United States Patent
Huang et al.

(10) Patent No.: US 6,190,041 B1
(45) Date of Patent: Feb. 20, 2001

(54) SHUTTER CONSTRUCTION OF A TYMPANIC THERMOMETER

(75) Inventors: James Huang; Kevin Lin, both of Hsinchu (TW)

(73) Assignee: Oriental Systems Technology, Inc., Hsinchu (TW)

(*) Notice: Under 35 U.S.C. 154(b), the term of this patent shall be extended for 0 days.

(21) Appl. No.: 09/327,478

(22) Filed: Jun. 9, 1999

(51) Int. Cl.[7] .............................. G01K 1/00; G01J 5/02; A61B 6/00
(52) U.S. Cl. ........................ 374/208; 374/131; 374/130; 374/133; 600/474; 128/664
(58) Field of Search ..................... 374/208, 133, 374/130, 131; 600/474; 128/664

(56) References Cited

U.S. PATENT DOCUMENTS

| | | | |
|---|---|---|---|
| 3,596,096 | * 7/1971 | Koehler | 73/355 R |
| 4,005,605 | * 2/1977 | Michael | 73/1 F |
| 4,797,840 | * 1/1989 | Fraden | 364/557 |
| 5,368,038 | * 11/1994 | Fraden | 128/664 |
| 5,991,652 | * 11/1999 | Barthelemy et al. | 600/474 |
| 6,001,066 | * 12/1999 | Canfield et al. | 600/559 |
| 6,115,107 | * 9/2000 | Nishi | 355/68 |

\* cited by examiner

Primary Examiner—G. Bradley Bennett
Assistant Examiner—Gail Verbitsky
(74) Attorney, Agent, or Firm—Bacon & Thomas, PLLC

(57) ABSTRACT

The shutter construction of a tympanic thermometer comprises a base formed with a horizontal groove and a vertical slot that communicate with each other, wherein said horizontal groove is for mounting a wave guiding duct; a supporting frame formed at the rear end of said base and formed with at least a first engaging portion and at least a second engaging portion; a shutter plate mounted in said vertical slot for closing said wave guiding duct; a linking element, the fore end of the linking element being coupled to the lower portion of said shutter plate and the rear end of the linking element being engaged with said first engaging portion of said supporting frame so that the fore end of the linking element can be swayed up and down relative to the rear end thereof; a spring element, the fore end of the spring element being coupled to said linking element; and an actuating element, the fore end of the actuating element being engaged with said second engaging portion of said supporting frame and the rear end of the supporting frame being coupled to the rear end of said spring element so that the rear end of said actuating element can be swayed up and down relative to the fore end of said actuating element, thereby said linking element can be moved down by said spring element when said actuating element is pressed down.

6 Claims, 8 Drawing Sheets

SHUTTER CONSTRUCTION OF A TYMPANIC THERMOMETER

FIELD OF THE INVENTION

The present invention relates generally to a tympanic thermometer, and more particularly, to the shutter construction of a tympanic thermometer.

BACKGROUND OF THE INVENTION

Clinical thermometers are very helpful in the diagnosis of diseases. The tympanic membrane is generally considered by the medical community to be superior to oral, rectal, or underarm sites for representing the body's internal temperature. The temperature of the tympanic membrane can be measured by detecting the infrared radiation from the tympanic membrane in the ear canal. In addition, the time needed for the body temperature measuring by using an infrared thermometer is short. The use of infrared thermometers therefore has become prevalent.

Referring to FIG. 1A, a tympanic thermometer is provided with a shutter mechanism for controlling the incoming of the infrared radiation from the tympanic membrane. When the elongated detection portion 11 is inserted into the external ear canal, the shutter mechanism is opened instantly to let the sensor 12 sense the infrared radiation in the ear canal and thereby the temperature of the tympanic membrane can be determined.

The shutter mechanism includes a base 13, a shutter plate 14, a mounting plate 15, a blocking element 16, a first linking element 17, a second linking element 18, a torsion spring 101, and a tension spring 102, wherein the base 13 is formed with a horizontal groove 131 and a vertical slot 132. The horizontal groove 131 is for mounting a wave guiding duct 103 and at the rear end of it is provided with a sensor 12. The shutter plate 14 is mounted within the vertical slot 132 of the base 13 and can be used to close the wave guiding duct 103. The mounting plate 15 is formed with a first, second, and third stubs 151, 152, 153, and a guiding portion 155. The blocking element 16 is pivotally mounted on the first stub 151. One end 161 of the blocking element 16 can prevent the shutter plate 14 from moving downward. One end of the first linking element 17 is engaged with and can only be moved horizontally in the groove 154. At the other end of the first linking element 17 is provided a push button 19 which can slide in the guiding through hole (not shown) of the guiding portion 155. The torsion spring 101 is mounted on the stub 152. One end of the torsion spring 101 is connected to the lower end of the shutter plate 14 and the other end abuts against a stub 171 formed on the linking element 17. The middle stub 181 of the second linking element 18 is telescopically engaged with the second stub 152. At one end of the second linking element 18 is provided a stub 182 pivotally connected with the first linking element 17 and at the other end is formed a snap groove 183 in which the end 162 of the blocking element 16 can be confined. One end of the tension spring 102 is connected to the third stub 153 and the other end to the first linking element 17.

With respect to the above prior art construction, referring to FIG. 1B, when the push button 19 is pressed, the first linking element 17 is moved horizontally and drives the second element 18 to pivot. In the meantime, the torsion spring 101 is twisted and accumulates energy. However, the shutter plate 14 will not move downward because it is blocked by the blocking element 16. Referring to FIG. 1C, when the second linking element 18 drives the blocking element 16 to pivot, the shutter plate 14 will be moved downward abruptly by the energy released from the torsion spring 101. When the push button 19 is released, the tension spring 102 causes the first linking element 17 to go back to its original position and the torsion spring 101 restores its original position and causes the shutter plate 14 to move upward and close the wave guiding duct 103.

The aforementioned prior art shutter construction achieves the shutter effect by means of a blocking element 16 and is provided with many parts. This incurs a high manufacturing cost.

SUMMARY OF THE INVENTION

The primary object of the invention is to provide the shutter construction of a tympanic thermometer which features a compact construction and a low manufacturing cost.

To achieve the above object, the shutter construction of a tympanic thermometer in accordance with the invention comprises a base formed with a horizontal groove and a vertical slot that communicate with each other, wherein said horizontal groove is for mounting a wave guiding duct; a supporting frame formed at the rear end of said base and formed with at least a first engaging portion and at least a second engaging portion; a shutter plate mounted in said vertical slot for closing said wave guiding duct; a linking element, the fore end of the linking element being coupled to the lower portion of said shutter plate and the rear end of the linking element being engaged with said first engaging portion of said supporting frame so that the fore end of the linking element can be swayed up and down relative to the rear end thereof; a spring element, the fore end of the spring element being coupled to said linking element; and an actuating element, the fore end of the actuating element being engaged with said second engaging portion of said supporting frame and the rear end of the supporting frame being coupled to the rear end of said spring element so that the rear end of said actuating element can be swayed up and down relative to the fore end of said actuating element, thereby said linking element can be moved down by said spring element when said actuating element is pressed down.

BRIEF DESCRIPTION OF THE DRAWINGS

The above and other objects and the features and effects of the present invention can be best understood by referring to the following detailed description of the preferred embodiments and the accompanying drawings, wherein.

DETAILED DESCRIPTION OF THE PREFERRED EMBODIMENTS

Figure 1A:
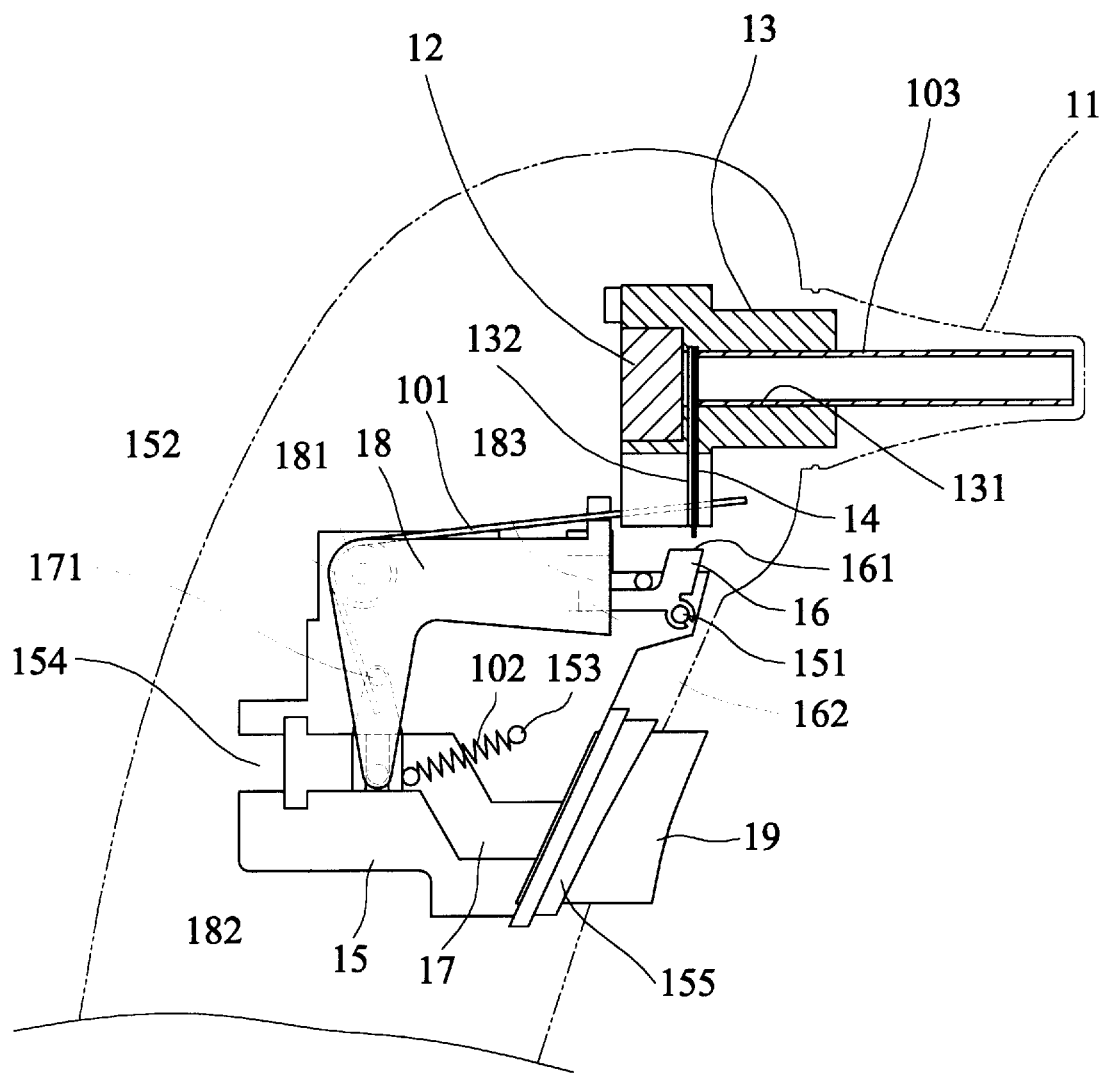
FIG. 1A is a schematic view illustrating the closed state of the shutter construction of a prior art tympanic thermometer.
Figure 1B:
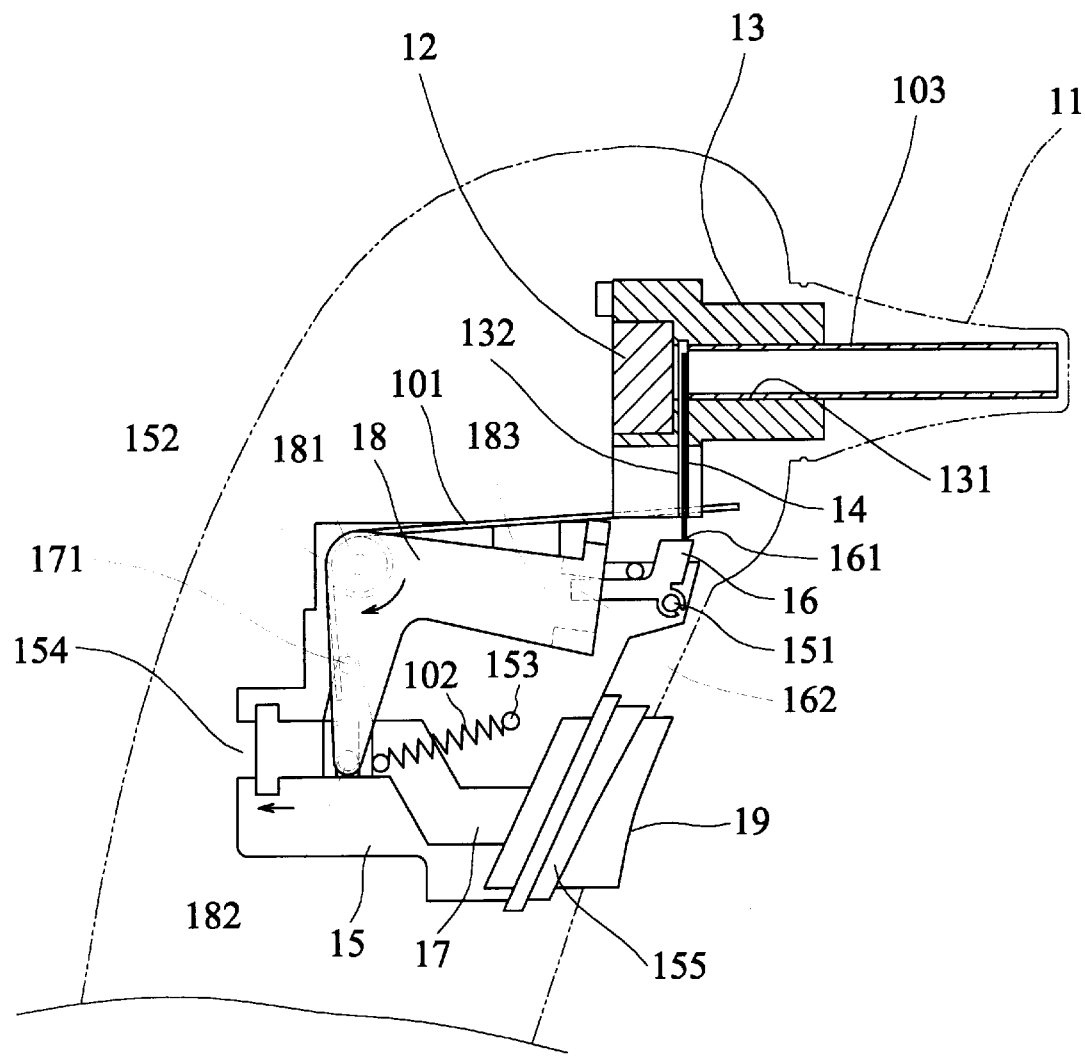
FIG. 1B is a schematic view illustrating the partly closed state of the shutter construction of the prior art tympanic thermometer.
Figure 1C:
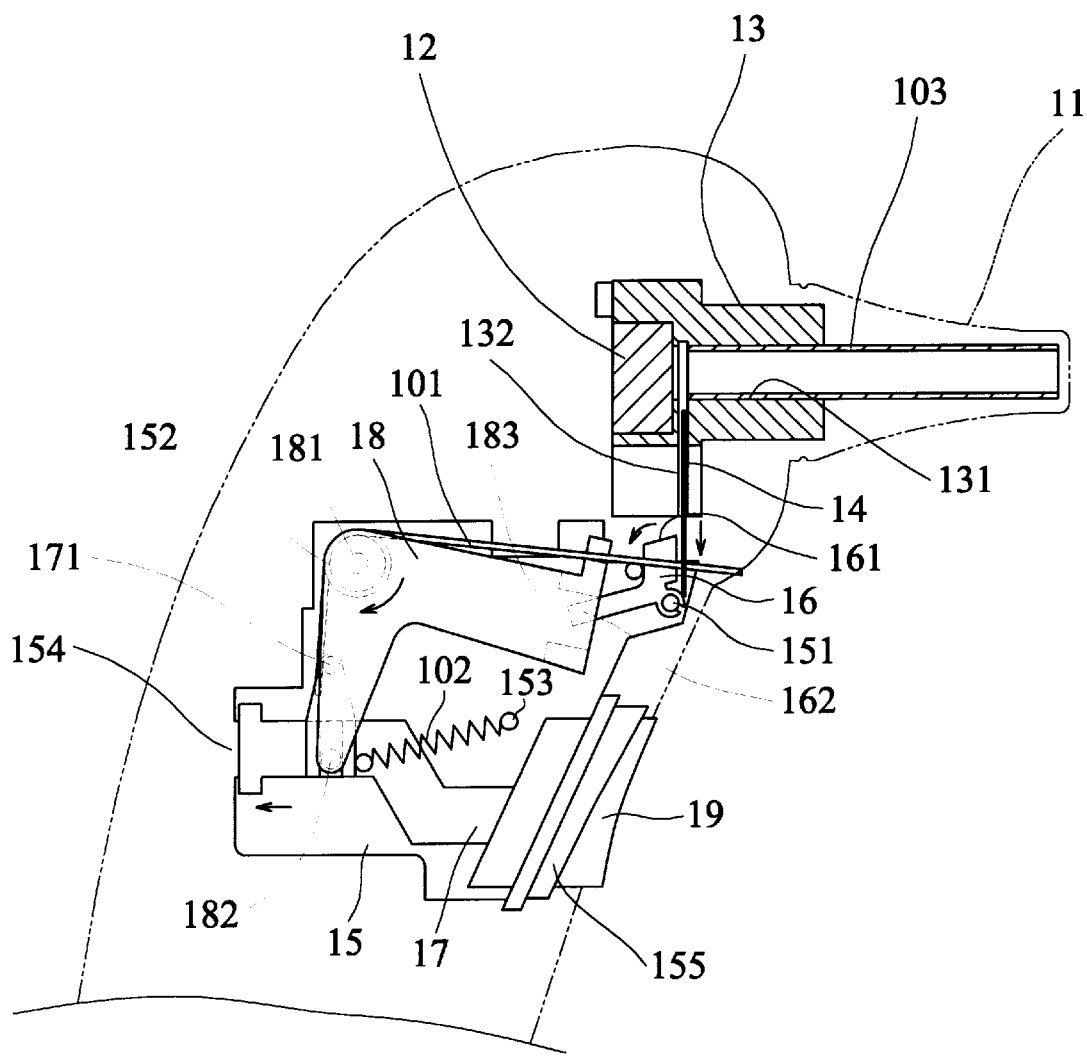
FIG. 1C is a schematic view illustrating the open state of the shutter construction of the prior art tympanic thermometer.
Figure 2:
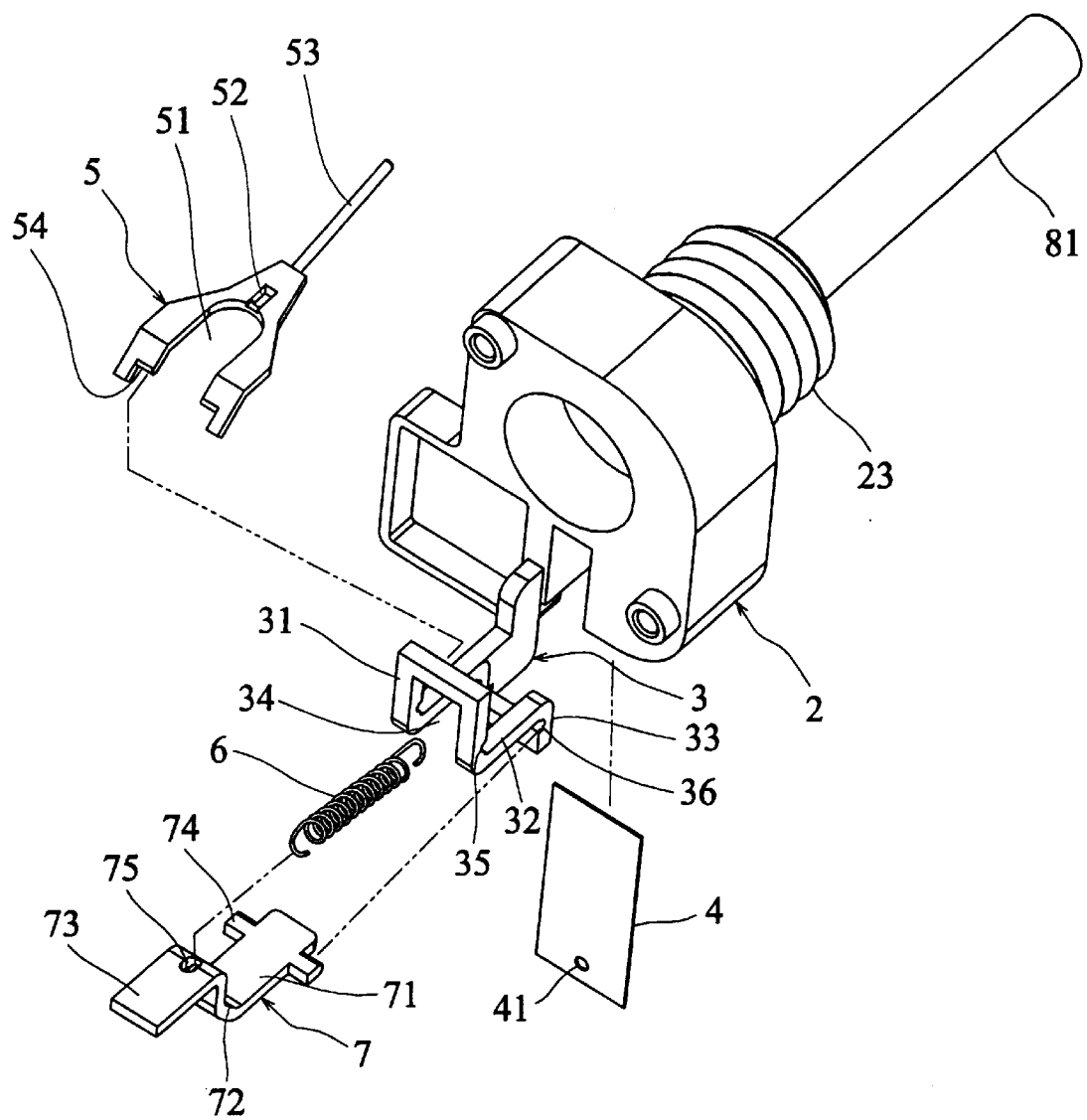
FIG. 2 is a perspective exploded view of a preferred embodiment of the invention.
Figure 3:
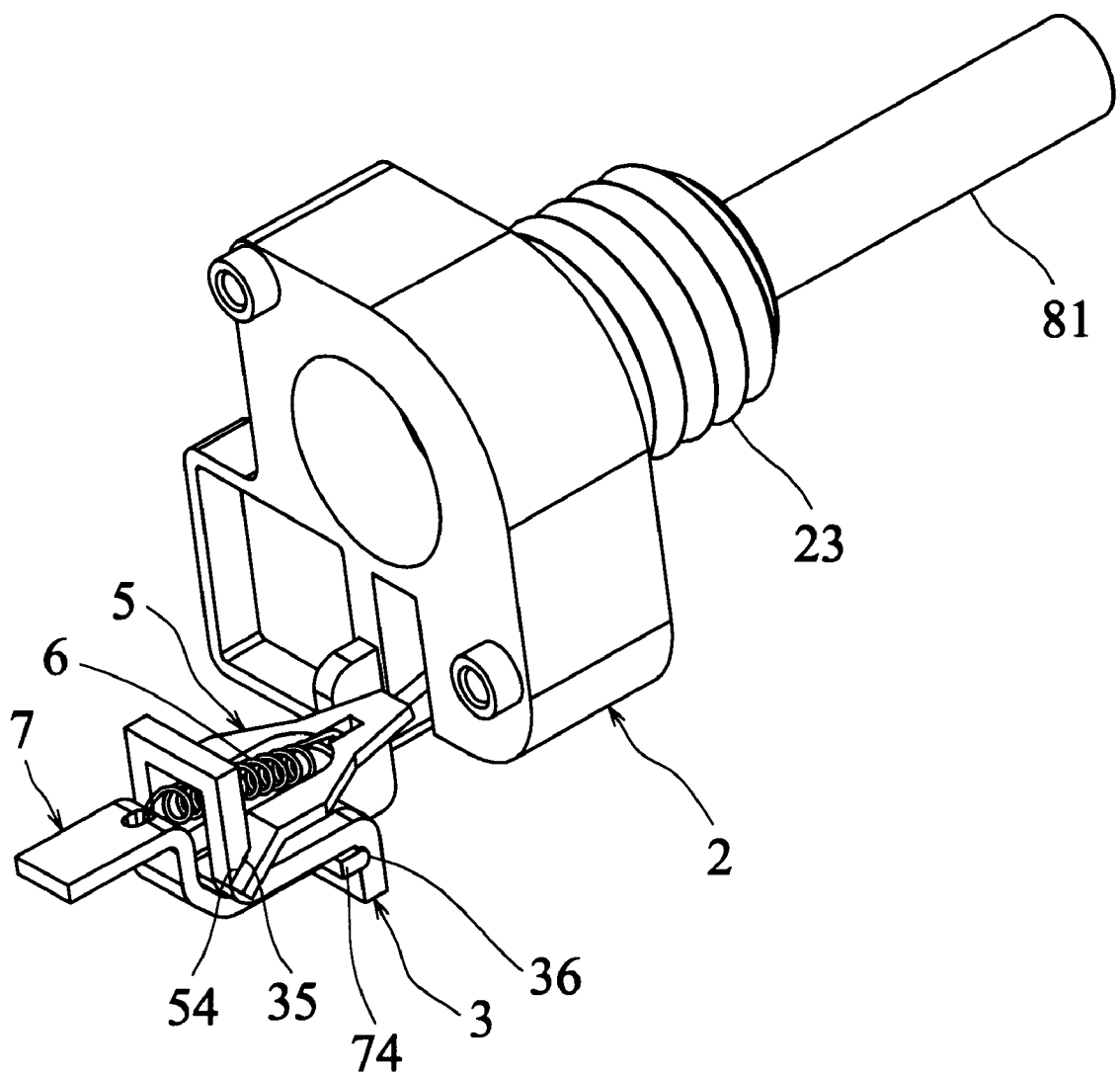
FIG. 3 is a perspective assembly view of the preferred embodiment of the invention.
Figure 4:
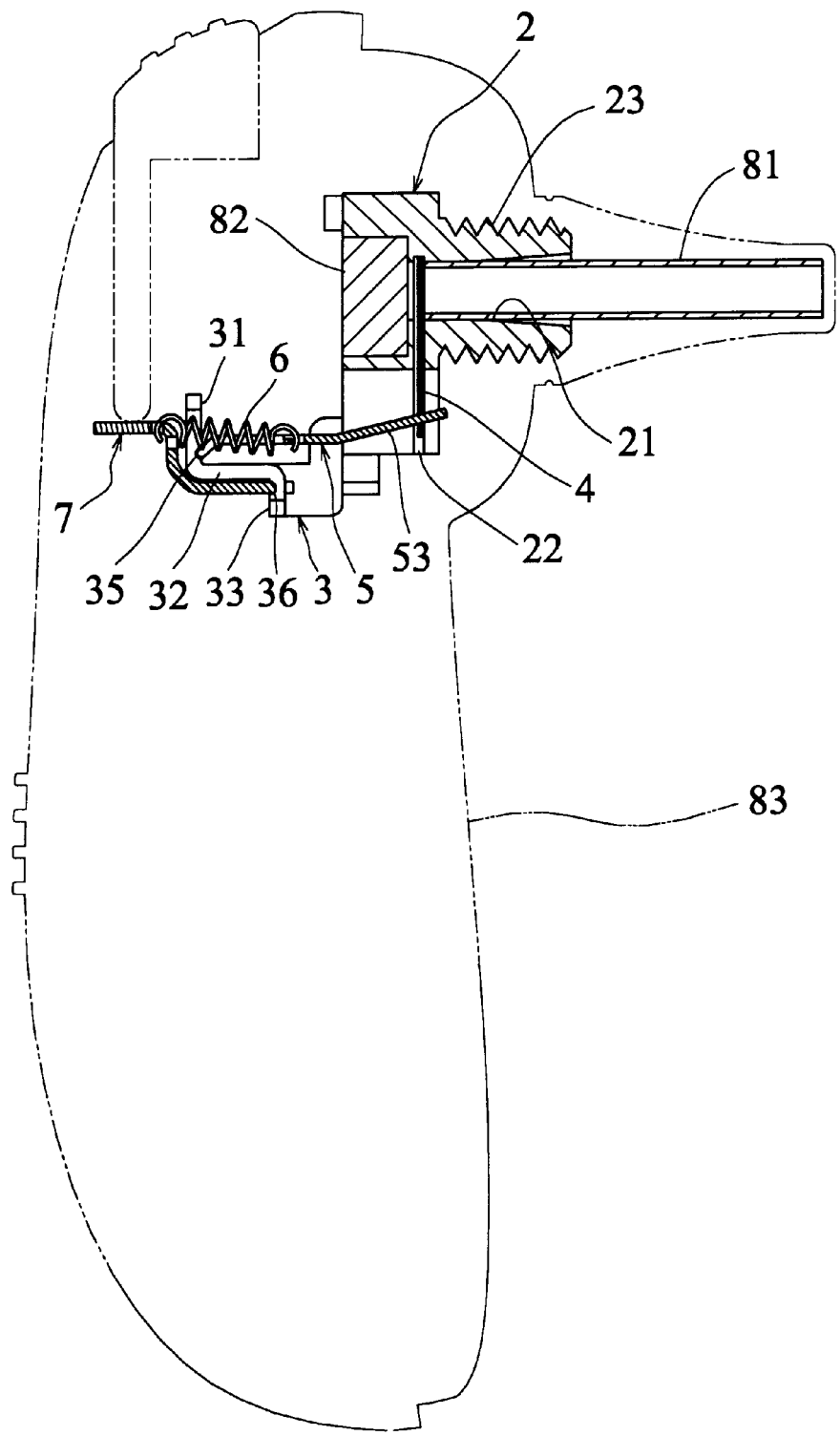
FIG. 4 is a sectional assembly view of the preferred embodiment of the invention wherein the shutter construction is in its closed position.

Referring to FIGS. 2, 3, and 4, the first embodiment of a shutter construction of a tympanic thermometer in accordance with the invention includes a base 2, a supporting frame 3, a shutter plate 4, a linking element 5, a spring element 6, and an actuating element 7.

The base 2 is formed with a horizontal groove 21 and a vertical slot 22 that communicate with each other. The horizontal groove 21 is for mounting a wave guiding duct 81. At the rear end of the base 2 is provided a sensor 82 and the fore portion of the base 2 is formed with an external thread 23 for threadedly engaging with the casing 83 of the tympanic thermometer.

The supporting frame 3 is integrally formed together with the base 2 in a casting process and is joined to the lower portion of the base 2 at the rear end thereof. The supporting frame 3 includes a horizontal section 32 and a first vertical section 31 and a second vertical section 33 provided respectively at the two ends of the horizontal section 32 and extending in opposite directions. In the middle of the supporting frame is formed a hollow portion 34. On the fore surface of each leg of the first vertical section 31 is formed a first round-shaped engaging groove 35. The first vertical section 31 is higher than the second vertical section 33. On the rear surface of each leg of the second vertical section 33 is formed a second round-shaped engaging groove 36.

The shutter plate 4 is mounted in a vertical slot 22 and can be used to close the wave guiding duct 81. At the lower portion of the shutter plate 4 is formed an engaging hole 41.

The linking element 5 is formed a U-shaped opening 51 at the rear central end thereof so that the spring element 6 can be moved through the U-shaped opening 51. In front of the U-shaped opening 51 is provided an engaging hole 52 and a linking rod 53. The fore end of the linking rod 53 is inserted into the engaging hole 41 of the shutter plate 4. At the read end of each of the two forks of the linking element 5 is formed an engaging surface 54 which is downwardly inclined at about 30 degrees and abuts against the corresponding first engaging groove 35 of the base 2 so that the fore end of the linking element can be swayed up and down.

The spring element 6 is a tension spring in this embodiment. The fore end of the spring element 6 is coupled to the engaging hole 52 of the linking element 5.

The actuating element 7 is formed with a vertical section 72. A first horizontal section 71 and a second horizontal section 73 connected to the two ends of the vertical section 72 respectively and extending in the opposite directions. The first horizontal section 71 is in a position lower than the second horizontal section 73. On each of the lateral sides of the first horizontal section 71 is formed an engaging stub 74 for abutting against the second engaging groove 36. In the second horizontal section 73 is formed an engaging hole 75 to which the rear end of the spring element 6 is coupled. The rear end of the actuating element 7 can be swayed up and down relative to the engaging stub 74.

Figure 5:
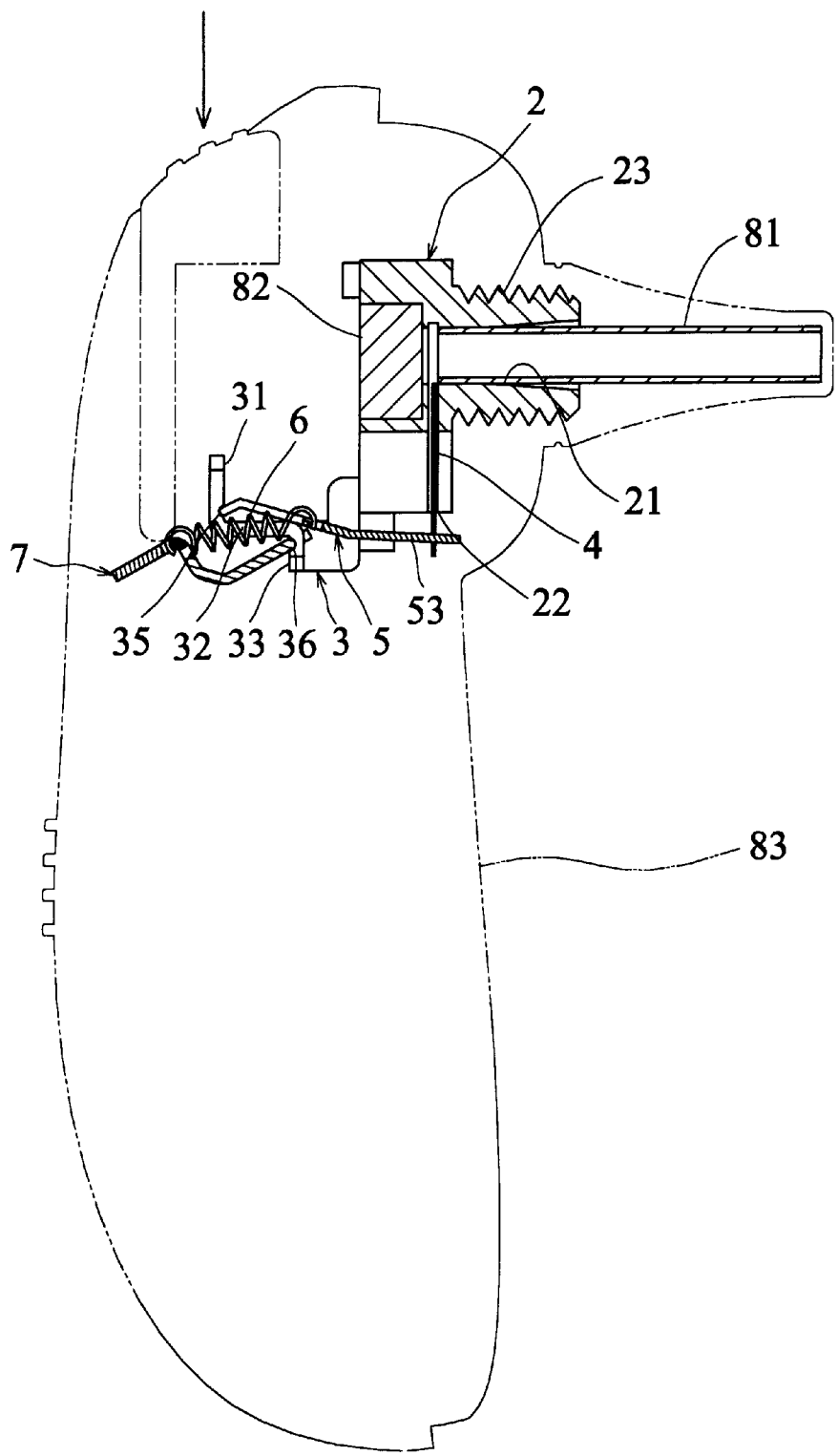
FIG. 5 is a sectional assembly view of the preferred embodiment of the invention wherein the shutter construction is in its open position.

With respect to the aforementioned construction, referring to FIG. 5, when the actuating element 7 is pressed down, the spring element 6 is elastically deformed in the first stage and is moved downward abruptly in the second stage, causing the linking element 5 together with the shutter plate 4 to be moved downward abruptly. When the actuating element 7 is released, the spring element 6 causes the linking element 5 to move back to its original position and the linking element 5, in turn, causes the shutter plate 4 to close the wave guiding duct 81 instantly.

From the above description, it can be seen that the shutter construction of the tympanic thermometer in accordance with the invention eliminates the blocking element and the torsion spring in the prior art and thus constitutes a compact construction that can achieve the efficacy of reducing the manufacturing cost.

Figure 6:
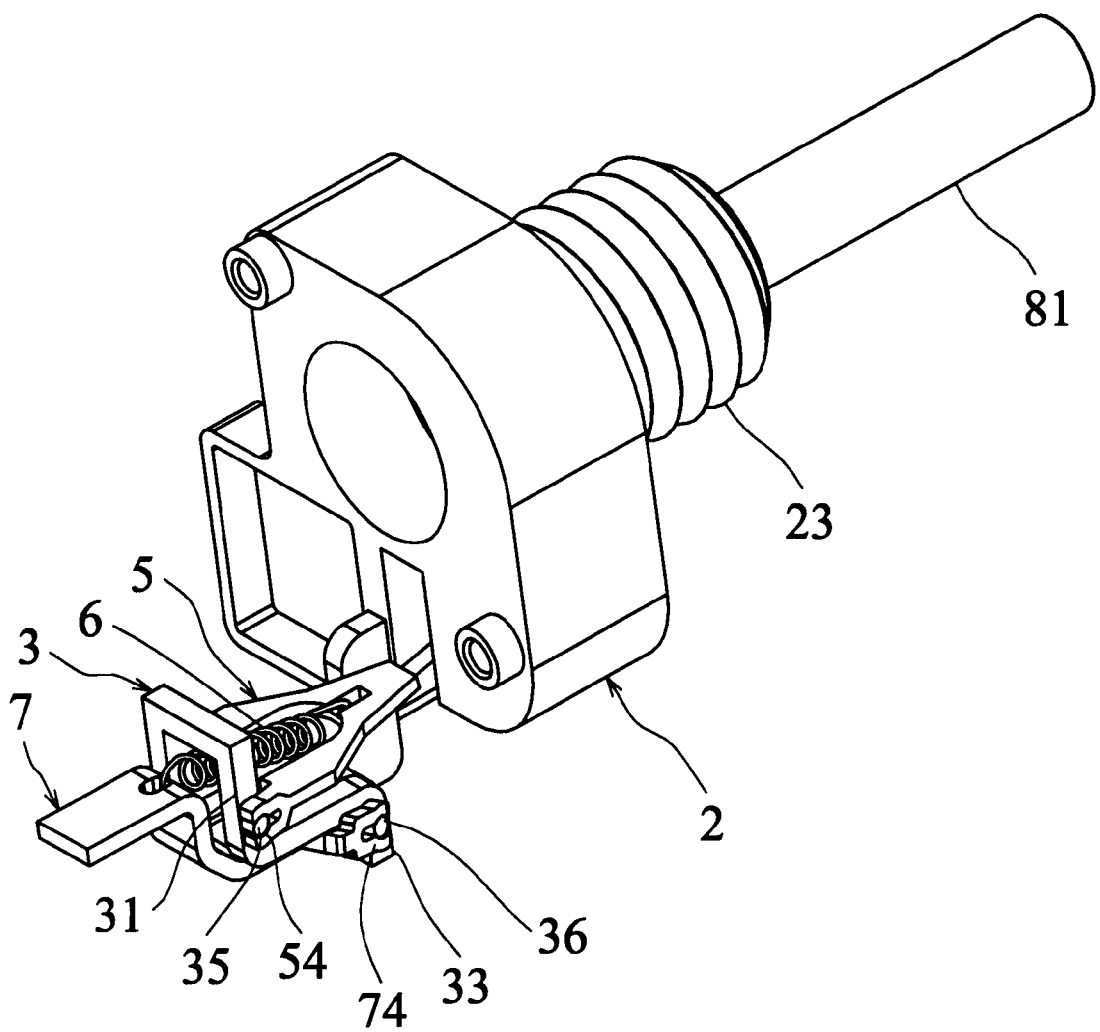
FIG. 6 is a perspective assembly view of another preferred embodiment of the invention.

A variation of the shutter construction in accordance with the invention is shown in FIG. 6. In this variation, the supporting frame 3 is provided with a first engaging stub 35 on each lateral side of the first vertical section 31 and provided with an engaging stub 36 on each lateral side of the second vertical section 33. On each lateral side at the rear end of the linking element 5 is provided a C-shaped engaging fork 54 for engaging with a corresponding first engaging stub 35. On each lateral side at the fore end of the actuating element 7 is provided a C-shaped engaging fork 74 for engaging with a corresponding second engaging stub 36.

Although two preferred embodiments of the invention have been illustrated and described, it will be obvious to those skilled in the art that various modifications may be made without departing from the scope and spirit of the invention defined by the appended claims.

What is claimed is:

1. A shutter construction of a tympanic thermometer comprising:
   a base formed with a horizontal groove and a vertical slot that communicate with each other, wherein said horizontal groove is for mounting a wave guiding duct;
   a supporting frame formed at the rear end of said base and formed with at least a first engaging portion and at least a second engaging portion;
   a shutter plate mounted in said vertical slot for closing said wave guiding duct;
   a linking element, the fore end of the linking element being coupled to the lower portion of said shutter plate and the rear end of the linking element being engaged with said first engaging portion of said supporting frame so that the fore end of the linking element can be swayed up and down relative to the rear end thereof;
   a spring element, the fore end of the spring element being coupled to said linking element; and
   an actuating element, the fore end of the actuating element being engaged with said second engaging portion of said supporting frame and the rear end of the supporting frame being coupled to the rear end of said spring element so that the rear end of said actuating element can be swayed up and down relative to the fore end of said actuating element, thereby said linking element can be moved down by said spring element when said actuating element is pressed down.

2. The shutter construction of a tympanic thermometer according to claim 1, wherein said supporting frame includes a horizontal section and a first vertical section and a second vertical section provided respectively at the two ends of the horizontal section and extending in opposite directions; in the middle of said supporting frame is formed a hollow portion; and said at least a first engaging portion is formed on said first vertical section and said at least a second engaging portion is formed on said second vertical section.

3. The shutter construction of a tympanic thermometer according to claim 1, wherein said linking element is formed a U-shaped opening at the rear central end thereof so that the spring element can be moved through said U-shaped opening.

4. The shutter construction of a tympanic thermometer according to claim 1, wherein said actuating element is formed with a vertical section; a first horizontal section and a second horizontal section are connected to the two ends of the vertical section respectively and extend in the opposite directions; said first horizontal section is in a position lower than said second horizontal section; on at least one lateral side of the first horizontal section is formed an engaging stub for abutting against said second engaging portion; and in said second horizontal section is formed an engaging hole to which the rear end of said spring element is coupled.

5. The shutter construction of a tympanic thermometer according to claim 1, wherein said base and said supporting frame are integrally formed.

6. The shutter construction of a tympanic thermometer according to claim 2, wherein both of said first engaging portion and said second engaging portion are in the form of a stub and are formed on at least one lateral side of said first vertical section and said second vertical section; said linking element is formed a U-shaped opening at the rear central end thereof so that said spring element can be moved through said U-shaped opening; on at least one lateral side at the rear end of said linking element is provided a C-shaped engaging fork for engaging with said first engaging portion; and on at least one lateral side at the fore end of the actuating element is provided a C-shaped engaging fork for engaging with a said second engaging portion.

\* \* \* \* \*